(12) United States Patent
Nickels

(10) Patent No.: US 6,942,647 B2
(45) Date of Patent: Sep. 13, 2005

(54) PINCH CLAMP COVER

(76) Inventor: William M. Nickels, 15886 Delta Ct., Brighton, CO (US) 80603

(*) Notice: Subject to any disclaimer, the term of this patent is extended or adjusted under 35 U.S.C. 154(b) by 0 days.

(21) Appl. No.: 10/292,826

(22) Filed: Nov. 12, 2002

(65) Prior Publication Data
US 2004/0092887 A1 May 13, 2004

(51) Int. Cl.$^7$ ................................................ A61M 5/00
(52) U.S. Cl. ..................................................... 604/250
(58) Field of Search ........................... 604/250, 30, 31, 604/32, 33, 34

(56) References Cited

U.S. PATENT DOCUMENTS

| | | | | |
|---|---|---|---|---|
| D213,849 S | * | 4/1969 | Sato | |
| 3,568,139 A | * | 3/1971 | Delzer | 439/759 |
| 3,831,625 A | * | 8/1974 | Roediger | 137/377 |
| 3,915,167 A | * | 10/1975 | Waterman | 604/250 |
| 4,453,295 A | * | 6/1984 | Laszczower | 251/10 |
| 4,553,963 A | * | 11/1985 | Young | 604/246 |
| 4,589,626 A | * | 5/1986 | Kurtz et al. | 251/10 |
| D333,518 S | * | 2/1993 | Gillette | |
| 5,775,325 A | * | 7/1998 | Russo | 128/205.12 |

* cited by examiner

*Primary Examiner*—Manuel Mendez
(74) *Attorney, Agent, or Firm*—Thomas W. Hanson

(57) ABSTRACT

A resilient cover for a pinch clamp which fully encloses the clamp providing a smooth, snag free surface. The cover pads the clamp and softens the sharp edges of the clamp, providing an increased level of comfort for the patient using the clamp. The cover also provides an increased level of safety by reducing the likelihood of the clamp being inadvertently opened or closed. The cover closely surrounds the clamp, restricting outward movement of portions of the clamp such as the latch and tongue, reducing the chance of their being accidentally released. Internal nubs extend into the cavity holding the clamp and engage the face openings of the clamp. In addition to holding the cover in place, the nubs resist inward movement of the latch and tongue reducing the chance of the clamp being accidentally engaged. The cover is slit along one side so that it can be placed over the clamp with the clamp positioned on a tube. The slit passes through one or more of the nubs. The nubs engage the clamp and help hold the slit closed. This eliminates the need for an external latch or other mechanism to hold the cover on the pinch clamp.

8 Claims, 3 Drawing Sheets

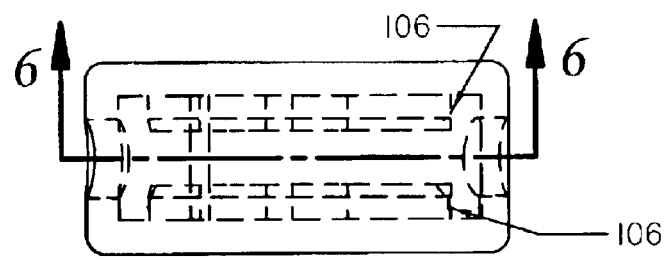
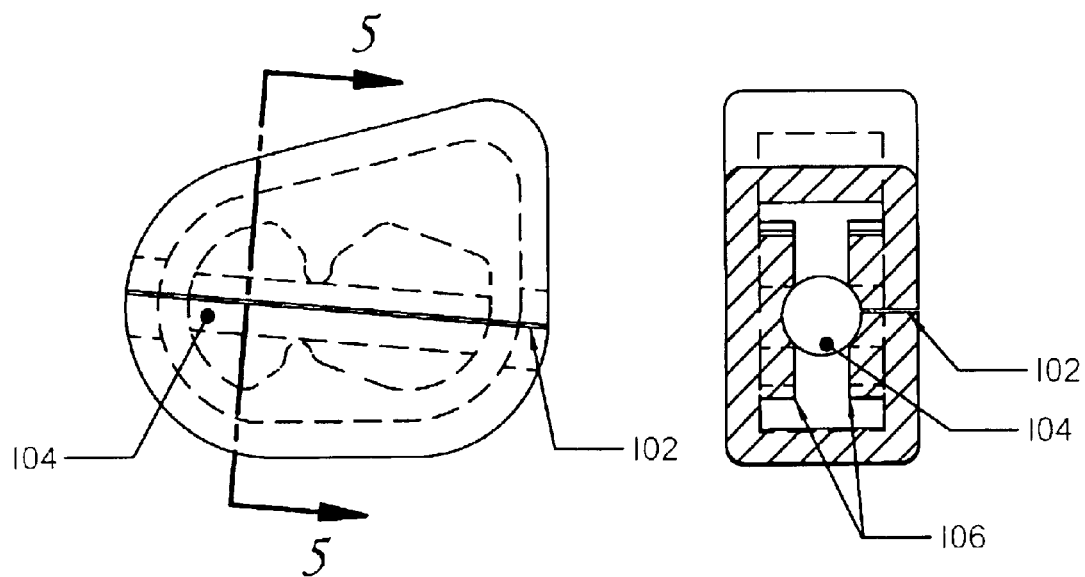

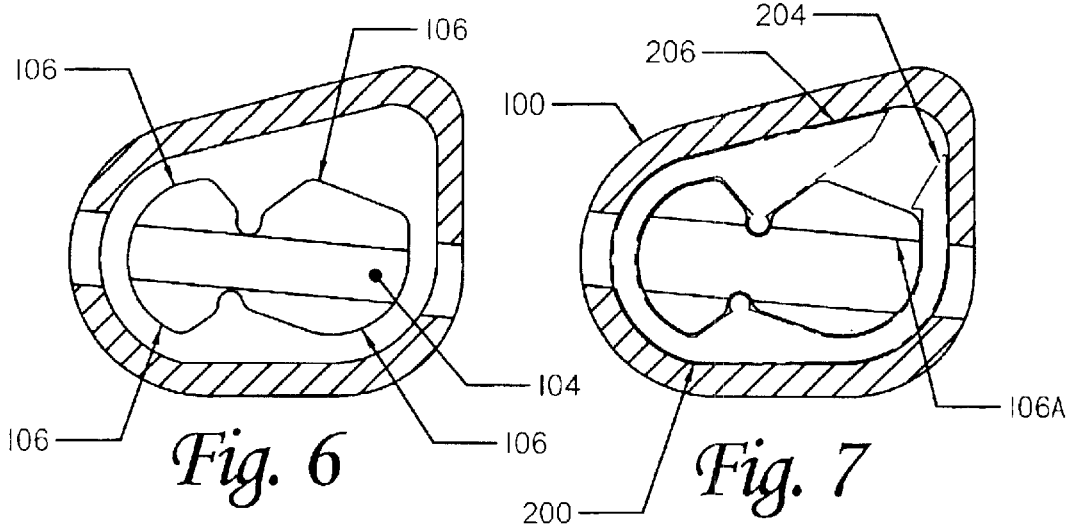
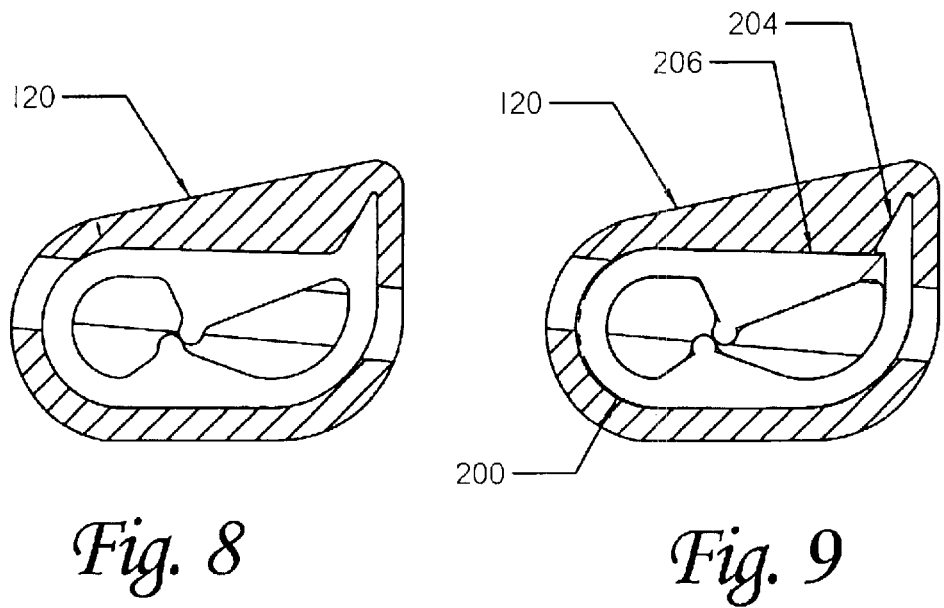

PINCH CLAMP COVER

BACKGROUND OF THE INVENTION

1. Field of the Invention

The present invention relates to the field of protective covers for pinch clamps, or similar, and specifically to such covers which are self retaining without the use of a separate latch.

2. Background Information

Medication and other fluids are often administered to patients intravenously via a flexible tube. Where it is desirable to regulate the flow of fluid through the tube, it is common to fit a pinch clamp to the tube. Where the administration is long term, the tube and pinch clamp may be affixed to the patient or their clothing on a semi-permanent basis, including while the patient sleeps.

Pinch clamps are simple, effective devices, but not without their problems. One is that they are hard and have relatively sharp edges. This can cause discomfort to the patient and can lead to bruising, especially where the patient lies on the clamp for extended periods, such as while sleeping. A second problem is that the clamp may snag on the patient's clothing, sheets, or other items in the surrounding environment. In addition to being an annoyance, this can pose a safety risk. Where the latch portion of the clamp snags, it may be released, inadvertently opening the pinch clamp. Less likely, but still possible, is that the clamp is accidentally compressed, inadvertently closing the clamp.

A typical approach to providing a cover for a pinch clamp would result in a bulky or heavy cover with an external latch to keep it in place. The latch would pose an additional risk of snagging while the weight and bulk would be annoying to the patient. Where the tube and clamp are attached to the patient or their clothing, weight must be kept to a minimum.

There is a need for a protective cover for a pinch clamp which pads the pinch clamp, softens the sharp edges, and presents a smooth, snag free surface. The cover should be light weight. Ideally the cover will be retained in position on the pinch clamp without the need for an external latch or other retaining mechanism. It is also preferable that it be possible to apply and remove such a cover without having to thread the cover over the tubing.

BRIEF SUMMARY OF THE INVENTION

The present invention is directed to an apparatus which encloses a pinch clamp, padding it and protecting the patient from its sharp edges.

According to the invention there is provided an enclosing shell surrounding a cavity in the shape of the pinch clamp to be covered. A passage through the shell accommodates the tube to which the clamp is attached and an opening allows the cover to be placed over the clamp while it is in position on the tube.

According to an aspect of the invention the enclosing shell so closely encloses the clamp that its latch can not easily move outward, effectively holding the latch in position, keeping the clamp either closed or open.

According to another aspect of the invention nubs project into the cavity holding the clamp and mate with openings in the face of the clamp. This helps retain the cover in position on the clamp and, further, the nubs block inward movement of the tongue portion of the clamp, effectively preventing the clamp from being inadvertently closed.

Further in accordance with the invention the opening for inserting the clamp is a slit in the side of the cover, passing through the nubs on that side. The nubs then also hold the edges of the slit, and thus the opening, closed.

The advantages of such an apparatus are a light weight, smooth, soft cover which pads the clamp and prevents the clamp from snagging. The cover may also serve to keep the clamp in a particular position, either open or closed depending on the embodiment, by resisting movement of the tongue and/or latch. The cover may also be manufactured to allow free movement between open and closed positions.

The above and other features and advantages of the present invention will become more clear from the detailed description of a specific illustrative embodiment thereof, presented below in conjunction with the accompanying drawings.

BRIEF DESCRIPTION OF THE SEVERAL VIEWS OF THE DRAWINGS

FIG. 3 is a top view of the cover.

FIG. 4 is a front view of the cover.

FIG. 5 is a cross section through the cover in a plane substantially perpendicular to the tubing passage.

FIG. 6 is a cross section through the cover in a plane substantially parallel to the front face.

FIG. 7 is a cross section in the same plane as FIG. 6 showing the pinch clamp positioned within the cavity of the cover.

FIG. 8 is a cross section through an alternative embodiment intended for use with a closed clamp, in the same plane as FIG. 6.

FIG. 9 is a cross section in the same plane as FIG. 8 showing the closed pinch clamp positioned within the cavity of the cover.

DETAILED DESCRIPTION OF THE INVENTION

Figure 1:
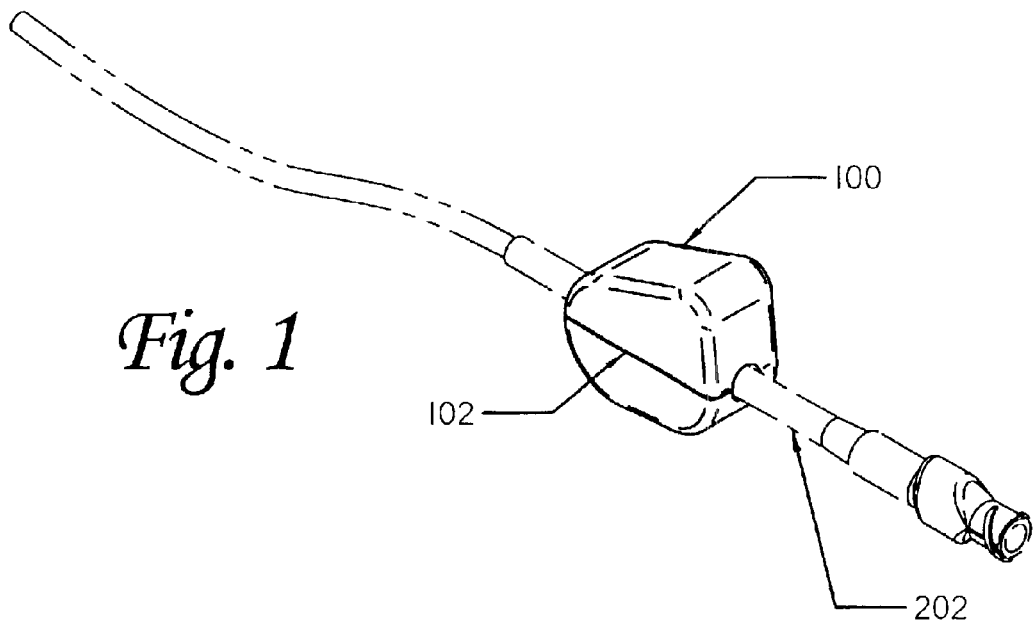
FIG. 1 is a perspective view of the cover in position on a clamp and tube.

The following discussion focuses on the preferred embodiment of the invention, a cover for a pinch clamp used for administering medication. However, as will be recognized by those skilled in the art, the disclosed method and apparatus are applicable to a variety of situations in which covering, protecting, or restricting access to a pinch clamp, or similar device, is desired.

Glossary

The following is a brief glossary of terms used herein. The supplied definitions are applicable throughout this specification and the claims unless the term is clearly used in another manner.

Cavity—space within the cover adapted to receive the pinch clamp.

Latch—that portion of the clamp which retains the tongue. Typically a flexible member having one or more teeth designed to engage the end of the tongue.

Nubs—internal projections which extend into the internal cavity of the cover and engage the openings in the face of the pinch clamp.

Pinch Clamp—generally a clamp used to pinch closed a tube or hose. May also be used to reduce the flow through the tube rather than stopping it completely. The embodiment of a pinch clamp illustrated herein is a common version but not exclusive. The inventive cover can be readily adapted for use with other types of clamps.

Slit—opening in the side of the cover allowing the clamp to be inserted into the cover.

Tongue—that portion of the clamp which engages the latch. Typically integral with the portion of the clamp which compresses the tubing, pinching off the flow of liquid.

Tubing passage—end-to-end opening through the cover which accommodates the tubing on which the pinch clamp is positioned.

Preferred Embodiment

The disclosed invention is described below with reference to the accompanying figures in which like reference numbers designate like parts. Generally, numbers in the 200's refer to prior art elements or elements in the surrounding environment while numbers in the 100's refer to elements of the invention.

Overview

The inventive pinch clamp cover is designed to fulfill a dual role of enhanced comfort and increased safety while being simple to operate. As an aid to comfort, the cover fully encloses the pinch clamp softening the sharp edges and providing a layer of padding. As a safety device, the cover reduces the chance of the clamp snagging on clothing or other items and reduces the chance of the clamp being inadvertently opened or closed.

The use of the internal nubs which engage the pinch clamp, in combination with the position and orientation of the slit, result in a cover which is securely retained on the pinch clamp without the use of a separate latch or retainer while still being easily removed. The elimination of a separate latch is important because it allows for a smooth outer surface with no protuberances.

The cover can be designed to hold the pinch clamp in either an open or a closed position, and this is anticipated to be its normal use. However, it can also be designed to accommodate both open and closed positions and even movement between these positions with the cover in place, if desired. The cover is sufficiently flexible and translucent to allow easy operation of the clamp without the need to open or remove the cover. If preferred, the cover can also be partially opened to operate pinch clamp or can be removed entirely.

Structure

The structure of the inventive cover is relatively straight forward, but that apparent simplicity is deceptive. The elements of the cover interact to provide an elegant solution which is not immediately obvious. Achieving a cover which is soft, flexible, and self-retaining is not easy.

Figure 2:
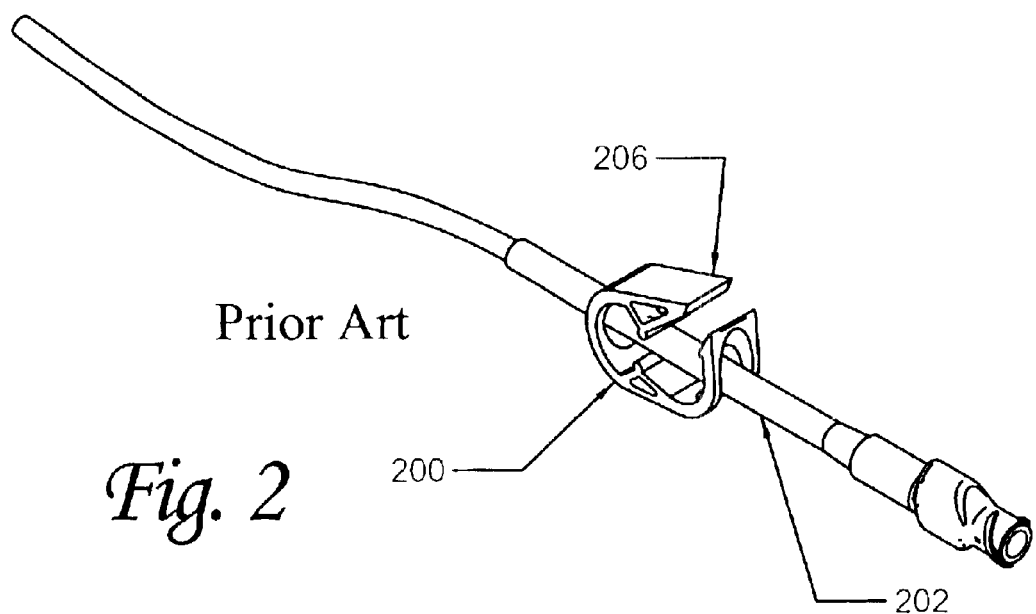
FIG. 2 is an illustration of an example prior art pinch clamp and tubing with which the cover might be used.

The external appearance of the cover, 100, is illustrated in FIG. 1 while the pinch clamp, 200, and tube, 202, to which it is fitted is shown in FIG. 2. Slit, 102, allows the cover to be opened, fit around the pinch clamp, and closed. All external corners are rounded to present a smooth, snag free surface. In the preferred embodiment, the outer shell of the cover is relatively uniform in thickness, providing approximately 0.10" padding over all surfaces of the clamp. Preferably this outer shell is a snug fit to the pinch clamp to aid retention of the cover on the clamp and to reduce movement of the cover.

The internal structure of the inventive cover is illustrated in FIGS. 3–7. The interaction of the cover, 100, with the pinch clamp, 200, is most clearly seen in FIG. 7 which is a cross section in the same plane as FIG. 6 but with the pinch clamp shown in position within the cover. As can be seen, the enclosing shell of the cover closely conforms to the outer profile of the pinch clamp. In addition to retaining the cover in position, this conformance limits outward movement of parts of the clamp. Specifically, the latch portion, 204, is restricted from moving outward. Because of the design of the clamp, it is necessary for the latch portion to move outward to either latch or unlatch the clamp. By restricting this movement, latching and unlatching becomes more difficult, and thus less likely to occur inadvertently.

Nubs, 106, also make it more difficult to inadvertently latch the pinch clamp. These nubs engage the openings in the face of the pinch clamp, 200. By occupying this space, the nubs make it difficult to close the pinch clamp. This is because closing the clamp requires that the tongue portion, 206, move inward, which would require compressing the nubs. The amount of resistance to closing the clamp can be adjusted by varying the hardness of the material used to manufacture the cover and the depth of penetration of the nubs. This is discussed below.

The nubs, 106, also serve a critical role in retaining the cover on the pinch clamp. By engaging and closely conforming to the face openings of the clamp, the nubs effectively grip the clamp, holding the cover in position. This is especially important on the side of the cover having the slit, 102. As shown in FIG. 5, the slit passes approximately through the center of the nubs, dividing them substantially in half. Each half grips part of the face opening of the clamp, and, in turn, is closely enclosed by the clamp. This cooperation holds the nubs in place, which in turn, holds the edges of the slit in place. The more deeply the nubs extend into the face openings of the clamp, the more firmly they are held in place. As can also be seen in FIG. 5, the preferred embodiment has a space between the nubs on opposing sides of the cover. The size of this space can be adjusted, or even eliminated, to alter the gripping power of the nubs. In practice the depth of penetration of the nubs would be coordinated with the flexibility of the material used, and its adhesion characteristics, to achieve the level of retention desired. Of course, the better the cover holds itself in place, the more difficult it is to remove when desired.

The positioning of the slit, 102, on the side of the cover, passing through the nubs, 106, is an important element in the design of the inventive cover. This orientation results in the nubs holding the slit closed. The slit will then not open by itself and the edges of the slit are less likely to snag on clothing or other items, pulling the slit open. Other orientations of the slit were tried, including the more obvious choice of placing the slit on the top so that the cover would open in a clamshell manner. Such an arrangement was found to be far more likely to open by itself, requiring a supplemental latch to hold the cover in place. Slitting the cover on the side, through the nubs, provides sufficiently secure retention that a supplemental latch or other closure is not needed. This allows for a cover which has a completely smooth outer surface and is simpler and less expensive to manufacture.

Tubing channel, 104, passes through the cover, oriented to receive the tubing, 202, to which the pinch clamp, 200, is attached. Its position and orientation would generally match the normal path of the tubing through the pinch clamp although the flexibility of the tubing allows for a range of possible orientations.

As illustrated, the side slit, 102, and the tubing passage, 104, are oriented at a slight angle to the adjacent edge. This is done to approximate the angle at which the tubing passes through the clamp when the clamp is open. If desired, the tubing channel and/or slit could be made parallel to this edge or oriented at a variety of other angles without effecting the performance of the cover. While the side slit would generally be aligned with the tubing passage, this is not required.

Materials

Selection of the material to be used in manufacturing the cover is important because its characteristics directly impact the performance of the cover. However, this importance should not be interpreted as mandating any particular material. A variety of materials are applicable and the process of selecting one which provides the desired characteristics is well known in the art.

Probably the most important characteristic is its durometer. The role of the cover in increasing comfort by padding the pinch clamp suggests a relatively soft material. However, the ability of the cover to retain itself in position on the clamp argues for a relatively stiff material. These competing requirements must be balanced against each other. In practice a durometer in the range of 30–40 on the Shore A hardness scale has been found to perform well in most situations. Clearly situations in which retention is more important (i.e. emergency rescue) or less important (i.e. a sedentary patient) could lead to use of materials with durometers outside of this range.

Another important characteristic is density, or specifically weight, of the finished product. The tubing and clamp to which the cover will be attached is often hanging from the patient in some manner, such as by being attached to their clothing. Increasing the weight of the combination may well cause irritation to the patient. As such, the cover should be as light as reasonably possible.

Preferably the cover would be translucent so that the position of the pinch clamp may be visually verified without opening the cover. It should also be possible to sterilize the cover using either heat, ultraviolet, chemical, or other applicable processes. This would be especially important where it is used in a hospital or group care environment.

In practice, insert molding with urethane has been found to be a good method of manufacturing the inventive cover. Urethane has good wear characteristics, grips the clamp well without being too sticky, and can easily be formulated to achieve the desired durometer. Silicon has also been used and performs adequately. Other materials are clearly also applicable.

Alternative Embodiments

The following discussion presents alternative embodiments which offer various advantages in structure or functions without departing from the principles of the invention.

FIGS. 8 and 9 illustrate an alternative embodiment, 120, of the present inventive cover which is designed to hold the pinch clamp, 200, in a closed position. The cavity matches the shape of a closed clamp, and the outer shell inhibits outward movement of the latch portion, 204, and tongue portion, 206, of the clamp. By restricting movement of the latch portion, likelihood of the clamp being released is reduced. Restricting outward movement of the tongue portion holds the clamp closed even if it is released and may allow the clamp to re-latch automatically.

A cover which allows movement of the clamp between open and closed positions would also be easily achieved. An outer shell which accommodates the greatest anticipated outward movement of the latch and tongue portions, similar to that of the preferred embodiment, combined with reduced size nubs to accommodate the greatest anticipated inward movement, similar to that of the above alternative embodiment, should suffice.

While the preferred form of the invention has been disclosed above, alternative methods of practicing the invention are readily apparent to the skilled practitioner. The above description of the preferred embodiment is intended to be illustrative only and not to limit the scope of the invention.

I claim:

1. A cover for a pinch clamp positioned on a tube, said cover comprising:
   a) an enclosing shell defining an internal cavity adapted to receive the pinch clamp;
   b) said shell having a passage therethrough adapted to receive the tube;
   c) said shell having an opening to said cavity whereby the clamp and tube may be inserted into said cavity; and
   d) wherein said clamp has face openings and said cover has at least one nub extending inward into said cavity and adapted to engage one of the face openings.

2. The cover of claim 1 wherein said nub substantially limits inward movement of the pinch clamp.

3. The cover of claim 1 wherein said opening comprises a slit defined to pass through said nub.

4. A cover for use with a pinch clamp having a latch, tongue, and face openings and adapted for positioning on a tube, said cover comprising:
   a) an enclosing shell defining an internal cavity adapted to closely receive the pinch clamp, whereby outward movement of at least one of the latch and tongue is significantly restricted;
   b) plural nubs extending inward into said cavity and adapted to engage the face openings in the clamp; and
   c) said shell having an opening into said cavity whereby the clamp and tube may be inserted into said cavity.

5. The cover of claim 4 wherein said opening comprises a slit defined to substantially bifurcate at least one of said nubs, each portion of said nub adapted to engage the clamp and hold said slit closed.

6. The cover of claim 5 wherein said nubs substantially limit inward movement of at least one of the clamp's latch and tongue.

7. The cover of claim 6 wherein said shell has a passage there through adapted to receive the tube and said slit is substantially aligned with said tube passage.

8. The cover of claim 7 wherein said cover is constructed of a resilient material having a Shore A hardness scale durometer in the range of 30–40.

* * * * *